United States Patent
Oleskow

[11] Patent Number: 5,916,439
[45] Date of Patent: Jun. 29, 1999

[54] ADVANCED SAFE WATER TREATMENT SYSTEM

[75] Inventor: Brett Oleskow, Elgin, Ill.

[73] Assignee: Safe Water Technologies, Inc., Elgin, Ill.

[21] Appl. No.: 08/819,869

[22] Filed: Mar. 18, 1997

[51] Int. Cl.⁶ .................................................. B01D 35/00
[52] U.S. Cl. ...................... 210/198.1; 210/206; 210/256; 210/266; 210/443
[58] Field of Search ................................ 210/192, 198.1, 210/202, 206, 209, 232, 244, 256, 266, 284, 748, 443

[56] References Cited

U.S. PATENT DOCUMENTS

| | | | |
|---|---|---|---|
| 3,342,335 | 9/1967 | Gamundi et al. | 210/244 |
| 3,551,091 | 12/1970 | Veloz | 210/192 |
| 4,615,799 | 10/1986 | Mortensen | 210/192 |
| 4,849,100 | 7/1989 | Papandrea | 210/192 |
| 4,948,505 | 8/1990 | Petrucci et al. | 210/282 |
| 4,971,687 | 11/1990 | Anderson | 210/256 |
| 4,995,976 | 2/1991 | Vermes et al. | 210/266 |
| 5,026,477 | 6/1991 | Yen | 210/198.1 |
| 5,501,801 | 3/1996 | Zhang et al. | 210/748 |
| 5,536,395 | 7/1996 | Kuennen et al. | 210/192 |
| 5,597,482 | 1/1997 | Melyon | 210/232 |
| 5,643,444 | 7/1997 | Garrigues et al. | 210/266 |
| 5,725,757 | 3/1998 | Binot | 210/192 |

*Primary Examiner*—Jay H. Woo
*Assistant Examiner*—Betsey J. Morrison
*Attorney, Agent, or Firm*—Maksymonko & Slater

[57] ABSTRACT

A water purification system for home or light commercial application including a preconditioning stage followed by an integrated water sterilization stage. Both stages utilize a single pressure chamber in which the active medium for the preconditioning stage is placed within this chamber as is the entire sterilization stage. More specifically, UV sterilization is contemplated with the UV stage having a stainless steel vessel which, however, is operated at zero differential pressure. A single head is fitted to the top of the pressure chamber and serves multiple functions of admitting the water to be purified and expelling the purified water and, further, to retain the UV vessel, the UV lamp and quartz shield. A segregation device is positioned at the inlet to the UV vessel to separate the respective stages and to assure that none of the preconditioning medium is admitted to the UV vessel.

5 Claims, 3 Drawing Sheets

ADVANCED SAFE WATER TREATMENT SYSTEM

BACKGROUND OF THE INVENTION

The present invention relates to the of field of water treatment and, more particularly, to systems for the purification of drinking and other water for use in homes as well as small office and commercial applications.

Purification contemplates a broad-range of technologies that necessarily address an equally broad litany of water quality problems. Often resort must be made to multiple technologies in furtherance of an overall water quality objective. The present invention falls within this latter category.

Purification issues range from the merely cosmetic—does the water look pure—to the health-compromising—does the water contain typhoid, dysentery, or other potentially harmful bacteria. And in between, there is the panoply of aquatic aggravations which, while non-lethal, often constitute more than minor annoyances. This latter group includes mineral-laden hard water (e.g. calcium and magnesium) and water with its own unique attributes of taste and smell (e.g. the hydrogen sulfide 'rotten egg').

Most commercially available home and small office water 'treatment' devices, including conventional water softeners and the plethora of activated charcoal and similar filters, have been largely directed to the water aesthetics arena. In short, these systems are designed to treat purification issues in connection with existing potable water supplies.

Water aesthetics is certainly not a trivial concern. Yet in recent years the focus has enlarged. Drinking water quality has become an increasing obsession for many homeowners even where the existing tap water supply (well or municipal) meets or exceeds minimum health standards. Mere 'pretty' or 'safe' water may no longer be sufficient. Bottled drinking water, therefore, has become increasingly popular—although its inconvenience and cost make it less than the optimal solution. The better long-term solution is the addition of permanent, on-site filtration or purification apparatus.

The present invention falls within this latter category of permanent, but after market apparatus directed to the further conditioning of water both for aesthetic as well as health reasons. Significantly, the present system may be employed not merely to improve the purity of certified 'safe' water supplies (i.e. in lieu of bottled water) but, in many areas, to condition otherwise non-potable water—rendering it safe for human consumption.

The present apparatus combines plural technologies in a unique arrangement that minimizes the overall size and complexity of the equipment required to achieve these stated purification goals while doing so in a manner that is substantially less expensive, cumbersome, and ungainly than the prior 'plumbed-together' collection of otherwise unrelated, independent purification sub-systems. These are important considerations in the home and small commercial environment where cost, required space, and sightliness are all factors to be weighed in selecting an overall water purification approach.

In the preferred embodiment, the present system employs a preconditioning stage that serves, in its own right, to remove or reduce unpleasant taste and odors, chlorine, pesticides, THM's, PCB's, and a variety of other chemicals not uncommonly found in water supplies, some potentially carcinogenic. Secondly, by reason of this preconditioning, suspended particulate and other chemical matter that might otherwise literally block the effectiveness of the subsequent disinfectant stage, are removed.

A variety of preconditioning stage sub-systems are contemplated hereby—the actual choice of filtering or other purification being determined by site-specific issues, i.e. the specific content or constituents of the water sought to be processed. Often, a filter comprising a bed of steam activated carbon is provided and sufficient. Alternatively, a conventional 'hard-water' softener may be employed.

Ultra-violet irradiation ("UV") forms the heart of the bacteriological purification, or follow-on, stage of the present apparatus. But, as noted, the efficacy of UV irradiation may be compromised, in the absence of the preconditioning stage, as contaminants may literally block full UV illumination of the water flowing past the lamp UV source.

The use of UV biological sterilization in combination with preconditioning filter equipment is not, itself, new. However, the conventional trade 'wisdom' has been to plumb-together, in cascade, existing and independent subsystems, such as activated charcoal filters, softeners, and/or UV or other sterilization equipment. While such combinations perform acceptably, they suffer the above-discussed shortcomings as to size, ungainliness, and, most importantly, the higher costs not-unexpectedly associated with the failure to take advantage of the efficiencies that accrue by an inventive integration of sub-technologies.

One such extravagance found with conventional cascade technology is the UV vessel, itself, which vessel must remain uncontaminated, as noted, to assure irradiation of all water flowing therethru. To achieve this desired level of continuing purity, polished stainless steel pressure vessels are commonly used. The stainless 'pressure' vessel must be designed to withstand up to 150 psi to accommodate the full range of standard water distribution pressures that may be encountered. It will be appreciated that elimination of the 'pressurization' requirement in connection with the stainless UV vessel represents a significant structural advantage both as to gauge (i.e. weight) and cost thereof.

The present apparatus achieves this goal by advantageously locating the UV vessel within a larger chamber, the latter chamber being pressurized to full system operating pressure. In this manner the UV vessel operates with a net-zero differential pressure (i.e. 'inside pressure' minus 'outside pressure'). At first blush this use of a secondary, outer pressure chamber might seem an extravagant and even more expensive means of eliminating the pressurization requirement of the UV vessel.

This would undoubtedly be true but for the fact that a pressure chamber is required in connection with the above-discussed preconditioning stage. The present invention advantageously integrates the UV subsystem within the preconditioning stage pressure chamber thereby, in essence, utilizing the preconditioning pressure chamber in a dual capacity—an efficiency utterly unknown to conventional cascade technologies.

Thus, the present invention contemplates but a single visible chamber substantially similar to the single tank that defines most existing filters. That there is a second vessel associated therewith is not, from a space and aesthetics perspective, apparent. Also 'absent' is the ungainly piping otherwise required to functionally plumb and interconnect multiple pressure chambers.

A coaxial arrangement is employed whereby the now, un-pressurized UV chamber is oriented along the longitudinal axis of the preconditioning pressure chamber. This coaxial arrangement is particularly advantageous by reason that a typical UV chamber need be of comparatively narrow diameter in order to assure that the entire water 'column' becomes properly irradiated (UV absorption and dispersion limit the effective 'thickness' of the water through which the UV may pass thereby correspondingly limiting the diameter of the UV vessel). Therefore, the placement of the UV chamber at the center of an otherwise conventional filter or softener pressure chamber or tank does not substantially lessen the cross-sectional area available for the preconditioning function. The preconditioning tank may be of any conventional fabrication, for example, fiberglass reinforced plastic.

A multipurpose inlet/outlet head is screwably fitted to the top of the preconditioning tank. This head serves not only to receive and distribute the inlet water across the top of the charcoal or other active medium in the preconditioning portion of the pressure chamber, but to channel the preconditioned and sterilized water effluent from the tank after it has been fully treated. Further, this head must provide a means for integrating and attaching the stainless UV chamber, the UV lamp; and the quartz tube that protects the UV lamp. And, yet further, this head must accommodate a 'sight means' for visually verifying operation of the UV lamp as well as a mechanism for removing the lamp for replacement, and the quartz tube for cleaning—all while maintaining proper pressure seals against the leakage of the pressurized water therefrom.

More specifically, the present head defines a multichannel/multi-port arrangement having a first fluid passage defined through and along the central axis of the head. A first port in fluid communication with this central passage serves as the actual water effluent interface from the present purification system. The stainless UV chamber is threadably interfaced to the lower portion of this central passage thereby rigidly mounting the chamber (to the head and pressure chamber) and providing a fluid path for the sterilized water from the UV chamber to the effluent port. A UV sight-gland is similarly screwably threaded to the top opening of the central passage and serves to physically lock the quartz tube in place and as a sight for confirming UV tube illumination.

A second passage or channel, in fluid communication with a second or inlet port, is provided in the head. This passage channels or sprays the incoming water around the inside periphery at the top of the pressure tank whereby the incoming water is distributed over the active filtering or other medium within the preconditioning portion of the present system. Thus, it will be appreciated that both inlet and effluent connections are made to the upper part of this single pressure chamber and, more specifically, through the above-described multifunction interface head.

The stainless UV vessel is dimensioned such that its lower distal end is spaced above the bottom of the pressure chamber approximately four inches. While it should be appreciated that other spacing dimensions may be used, this dimension has been found to be sufficient to allow placement of a UV vessel inlet filter at the lower end of the stainless UV vessel. This filter serves to segregate the first preconditioning chamber from the second, coaxially positioned UV sterilization vessel by literally blocking egress of the active medium from the first chamber into the UV vessel.

It is therefore an object of the present invention to provide a compact and comparatively inexpensive water purification system for home, small business or commercial use. A further object is to provide for water sterilization. Yet another object is to provide water preconditioning prior to sterilization. It is an object of the present invention that such preconditioning may be combined with the sterilization to minimize the number of pressure vessels required. It is an object of one embodiment of the present invention that UV irradiation shall be used for sterilization. It is therefore a further object that a non-pressurized stainless steel UV vessel be employed. And it is yet another object that such vessel be positioned within a pressure chamber which will therefore serve a dual capacity of providing water preconditioning and as a pressure housing for the the UV vessel. In one embodiment it is an object that a multifunction/multi-port head be fitted to the top of a single chamber. It is an object that the head provide an inlet and means for applying the inlet water onto the upper portion of filtration media within the single chamber. It is an object that the head provide an second effluent port, not in fluid communication with the inlet port, to receive sterilized and processed water from the chamber. Further, it is an object that the head include means for affixing a UV vessel thereto in fluid communication with the effluent port and means for accessing the UV lamp and protective quartz tube or sleeve associated therewith. It is an object of the present invention that the chamber include means for segregating the preconditioning portion of the system from the sterilization portion whereby charcoal or other active filtration media associated with the preconditioning portion of the system are prevented from entering the sterilization portion. These and other objects will become apparent from the drawings and specification which follow.

DESCRIPTION OF THE PREFERRED EMBODIMENT

Figure 1:
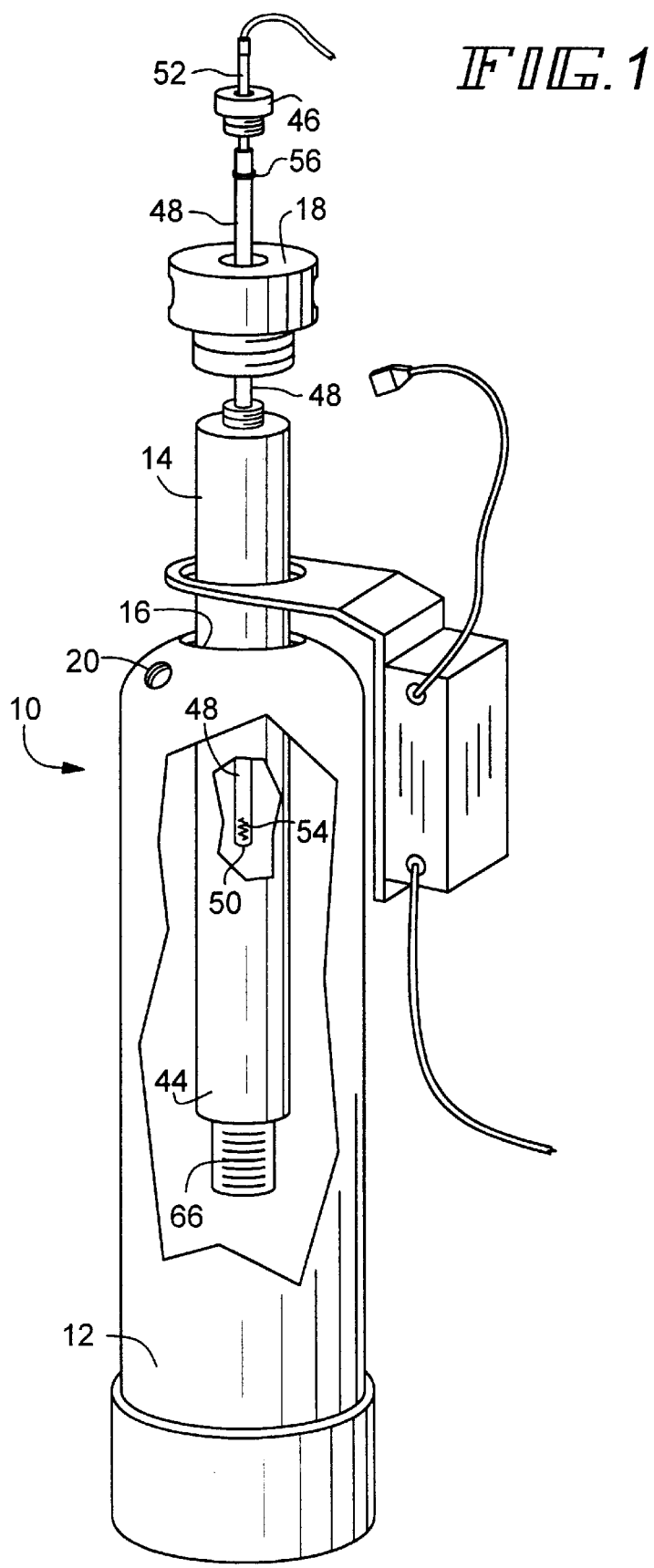
FIG. 1 is front elevation exploded view, with portions broken away, of a single chamber water purification system according to the present invention.

FIG. 1 best illustrates the single chamber embodiment of the water purification system 10 of the present invention, shown partially exploded and partially broken away to reveal details of the construction and, importantly, the dual-functionality and efficacy of the single fiberglass reinforced plastic chamber or tank 12. While the illustrated embodiment contains only a single tank 12, it will understood that additional external chambers may be incorporated, e.g. a water softener brine take, without departing from the dual chamber functionality, head design, and other efficiencies disclosed herein.

As is apparent from FIG. 1, tank 12 is of generally conventional design and size. And while the diameter of this tank may be increased consistent with the requirements of the preconditioning stage (discussed further below), such enlargement may not be required by reason that the dimensionally narrow UV sterilization vessel 14, positioned within tank 12 along the central longitudinal axis thereof, does not substantially lessen the remaining cross-sectional area available in the tank for the preconditioning function. One immediate benefit of the present arrangement, therefore, is the elimination of a separate UV subsystem which systems have, historically, been less than attractive and, in any event, require additional space and must be installed and 'plumbed' to the other preconditioning apparatus. In summary, from a space and appearance perspective, the multi-functional water purification system of the present invention may be contained in a single tank reminiscent of prior art unitary-function water processing filters/systems.

As noted, tank 12 is of generally conventional design. Virtually any pressure chamber may be used including metal or molded and wrapped fiberglass. A fiberglass reinforced plastic tank is preferred as the best compromise between cost and weight and, further, in view of the necessity of having two sealable access ports therein. Specifically, a first threaded aperture 16 is provided, through the top or dome of tank 12 centered on the longitudinal axis thereof, to receive the multiple channel/multi-port tank interface head 18. A second access aperture 20 is provided, generally at the top of the tank adjacent aperture 16, through which the activated charcoal or other preconditioning medium may be added or removed from the tank. This access aperture is ordinarily sealed by a screw-plug (not shown) during normal operation of the present water purification system.

Figure 2:
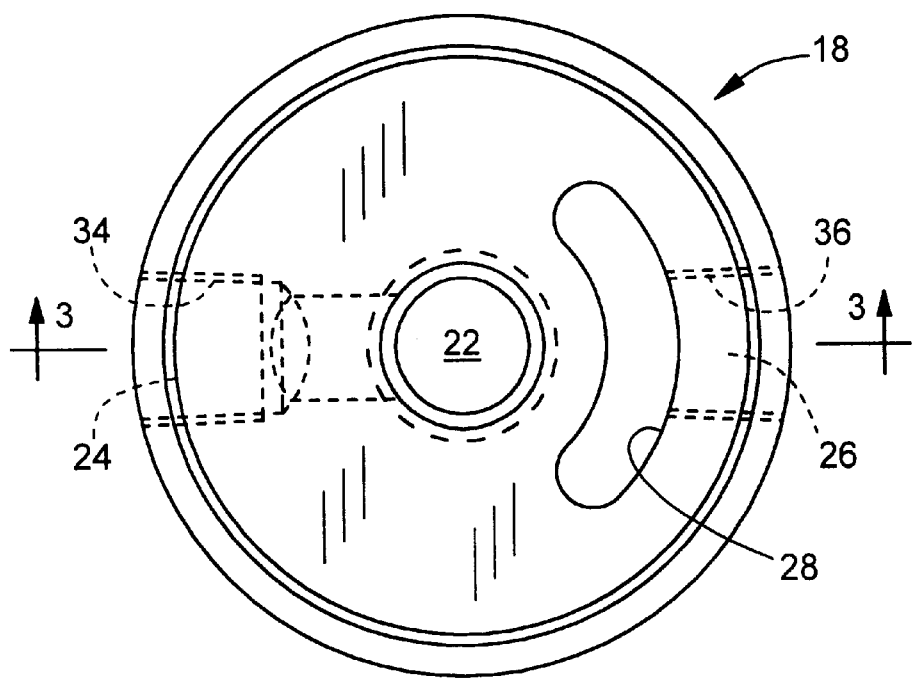
FIG. 2 is a top plan view of the tank interface head of the water purification system of FIG. 1.
Figure 3:
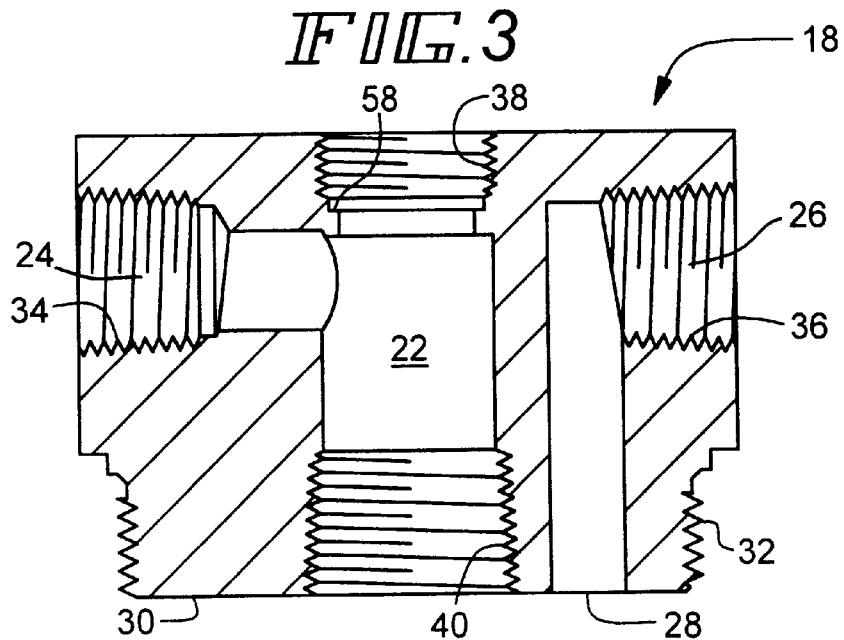
FIG. 3 is a front elevation view of the tank interface head taken in section along line 3—3 of FIG. 2.

FIGS. 2 and 3 best illustrate the tank interface head 18 of the present invention including an axial, cylindrical channel 22 extending the entire vertical length through head 18, a first effluent port 24 in fluid communication with channel 22, and a second inlet port 26 in fluid communication with an arcuate fluid spray aperture 28 disposed in the lower face 30 of the head. Threads 32 are provided at the lower end of head 18 which mate with corresponding threads in tank aperture 16, in turn, rigidly affixing head 18 in liquid-tight manner to the top of the head.

The effluent and inlet ports are each threaded at 34 and 36, respectively, to receive conventional water pipe or tube fittings (not shown). These ports are, as should be apparent, the sole fluid interface to the present apparatus. (However, it must again be stressed that alternative preconditioning equipment may be substituted for the straight filter arrangement disclosed herein and, consequently, additional plumbing, hardware, and controllers may advantageously be interfaced with the present apparatus including, for example, a hard-water softener brine tank and controller.)

Further, both the upper and lower distal ends of channel 22 are threaded at 38 and 40, respectively, for the purposes set forth hereinafter. Specifically, lower threads 40 receive the corresponding upper threaded fitting 42 of the stainless steel UV vessel 44 (FIG. 4) thereby rigidly attaching this vessel to head 18, in turn, positioning the UV vessel in fixed position within and along the central axis of tank 12.

The upper threads 38 of channel 22 receive a translucent, acrylic gland nut 46 (FIG. 1) which serves several functions. First, the gland nut sealingly retains a quartz tube or sleeve 48 within the UV vessel. As is well known, the UV lamp, which forms the heart of the UV sterilization function within the UV vessel, must be shielded from the often cold water that passes through the UV vessel. This is required both by reason that the UV lamp operates at elevated temperatures as well as the need to insulate and separate the lamp, electrically, from the water.

The quartz sleeve 48 defines a liquid-tight tube having a closed and sealed bottom at 50 into which UV lamp 52 may be removably positioned. A spring or similar device 54 is placed at the bottom of the quartz sleeve and serves, first, as a shock-absorber should the UV lamp be inadvertently dropped into the sleeve and, second, as a spacer to maintain the upper portion of the UV lamp above the gland nut 46 to permit access thereto.

Quartz sleeve 48 is received snuggly within channel 22 of the head. An O-ring 56 is positioned around the upper end of the quartz sleeve as shown in FIG. 1. This ring is received and seats on the annual lip 58 (FIG. 3) as the sleeve is inserted, through head channel 22, into the UV vessel. The gland nut 46 engages this O-ring as the gland-nut is screwably inserted into the head thereby compressing the O-ring which, in turn, seals the UV vessel (it being remembered that the interior of the quartz sleeve remains at atmospheric pressure while the water surrounding and passing by the sleeve is pressurized to full system pressure).

Upward movement of the quartz sleeve is further restrained by the gland nut which abuttingly contacts the sleeve's top thereby locking it against further upward travel. This butting engagement further serves as a mechanism for light conduction whereby UV light is transmitted from the sleeve into the translucent acrylic gland nut, in turn, serving as a visual indicator of continued UV lamp activity. In short, a bluish glow signals that the UV lamp is, in fact, illuminated and performing its sterilization function.

Finally, while the limited diameter of the central bore through the gland nut 46 precludes the upward travel of the quartz sleeve 48, the bore is of sufficient diameter to permit the passage of the UV lamp 52, itself. As the interior of the quartz sleeve 48 is free from water and remains at atmospheric pressure, it will be appreciated that the UV lamp may be freely removed, for replacement or otherwise, at any time without having to remove or bypass the present purification system or the water source thereto.

Figure 4:
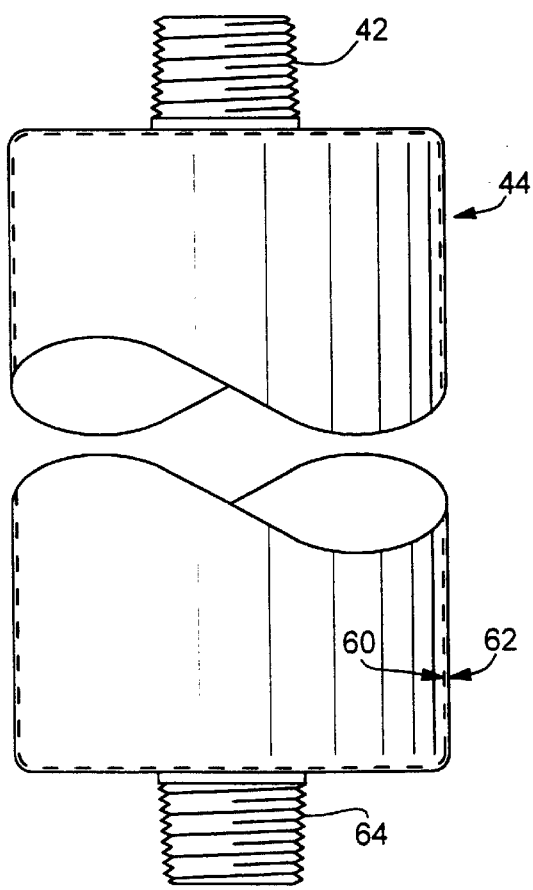
FIG. 4 is a front elevation view of the stainless steel UV vessel of the water purification system of FIG. 1.

FIG. 4 illustrates the UV vessel 44 of the present invention. This vessel is in the order of about 31 inches in length and 3.8 inches in diameter, although any vessel size may be utilized consistent with the desired UV irradiation and water flow rate requirements. As it is contemplated that the present system will find application as a 'whole-house' purification system, i.e. one that purifies the overall water source to a building as opposed to merely purifying a particular appliance or spigot location such as a drinking water tap, flow rates up to 10 gpm are contemplated. Irradiation dosage levels of 30,000 uW-sec/cm$^2$ are considered sufficient to kill most bacteria found in most water sources. The 'sizing' of UV sterilization systems is well known and forms no part of this invention.

What is significant to this invention is the fact that the UV vessel 44, while water-tight, need not operate at, nor withstand, the substantial differential pressures, e.g. up to 150 psi, required by stand-alone cascaded technology arrangements. More specifically, it will be understood that by reason of the positioning of UV vessel 44 within the interior of the preconditioning chamber 12, it is this latter chamber that must withstand these differential pressures. In short, as the same overall system pressure is impressed against both the interior and exterior walls 60 and 62, respectively, there is no differential pressure therebetween. In this manner a relatively less expensive, non-pressurized UV stainless steel vessel may be employed.

A second threaded fitting 64 is provided at the bottom of UV vessel 44 to receive the subsystem segregation interface device 66 which serves to delineate and separate the preconditioning function, i.e. around the perimeter of the main chamber 12 outside of vessel 44, from the UV sterilization of vessel, itself. As previously indicated, head 18 receives, through inlet 26, the yet-to-be-purified water source and causes that water to be sprayed, from the arcuate aperture 28, onto the top of the active medium (not shown) within chamber 12. This medium, depending on whether simple filtering or the more complex water-softening function is employed, may variously completely fill the interior of chamber 12 or a portion, generally more than half, thereof. In any event, the water literally trickles downwardly through the active medium of the preconditioning subsystem, around and adjacent the UV vessel.

Figure 6:
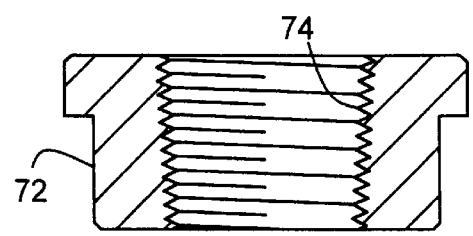
Figure 5:
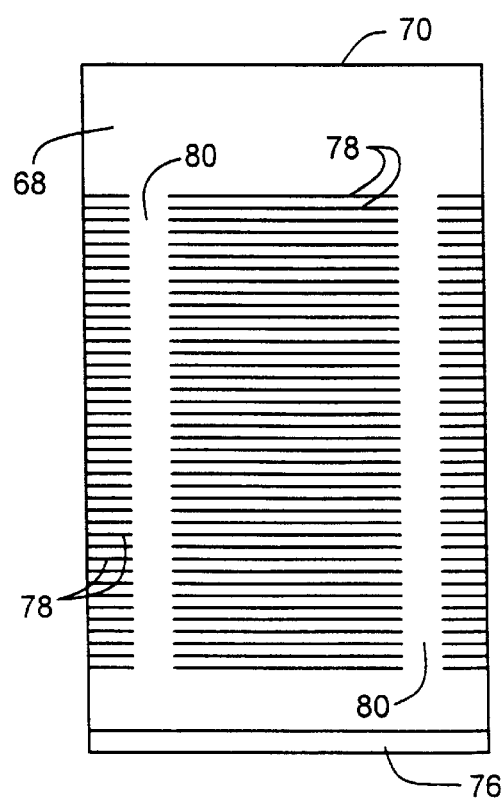
FIG. 5 is a front elevation view of the tubular member of the subsystem segregation interface of the water purification system of FIG. 1; and, FIG. 6 is a front elevation view, in section, of the UV vessel coupling member of the segregation interface of the water purification system of FIG. 1.

But in no event, can the active medium of the preconditioning portion of the present system be permitted to enter and contaminate the secondary UV sterilization system along with the now-preconditioned water which enters the UV vessel through its lower fitting 64. FIGS. 6 and 7 illustrate a preferred arrangement for segregation device 66. More specifically, a standard length of 2 inch PVC pipe 68, approximately 4 inches long, is, at its top end 70, cemented to a threaded bushing 72 which bushing has internal threads 74 that mate with, and are received on, the lower UV vessel fitting 64. A plug 76 is cemented to the lower end of pipe 68 to completely close-off this opening. A series of slots 78 are formed or cut into pipe 68 and serve to admit water from the lower portion of the preconditioning subsystem into the UV vessel while blocking the admittance of any of the active medium associated therewith.

The size and number of such slots must be selected to achieve, first, the required flow rate (at minimal pressure loss) and, second, to guaranty that the active medium or other particulate matter cannot enter the UV vessel. In the preferred arrangement of segregation device 66, for use with an activated charcoal preconditioning medium, 40 rows of slots, each slot being 0.01 inches in width and spaced $1/16''$ apart are provided. Further, each row preferably includes four partial slots spaced apart by longitudinal runners 80 to maintain the structural rigidity of device 68.

Referring again to FIG. 1, a power supply 82 is shown. This supply connects, and provides the requisite current, to UV lamp 52. Such supplies are well known and are not considered further herein.

While the preferred embodiments have been described, various alternative embodiments may be utilized within the scope of the invention which is limited only by the following claims and their equivalents.

I claim:

1. Integrated apparatus for purification of water, the integrated purification apparatus including a pressure chamber having an inlet to admit water thereto for purification and an effluent outlet for the discharge of purified water therefrom; said integrated purification apparatus further including preconditioning means and ultraviolet sterilization means; the ultraviolet sterilization means including an elongate vessel having first and second spaced apart means at respective opposed first and second ends thereof for entry of water to be sterilized and for the expulsion of water that has been sterilized, the sterilization vessel being located within the pressure chamber whereby a substantially zero differential water pressure shall be present thereon, the second spaced apart means for expulsion of sterilized water being in fluid-tight communication with the pressure chamber effluent outlet whereby no water may pass directly to the outlet from the inlet in the absence of the active preconditioning means media; the preconditioning means including active media for purifying water, the active media being located within the interior volume of the pressure chamber not otherwise occupied by the sterilization vessel; means for directing the water from the pressure chamber inlet onto the active media; segregation means at the first spaced apart means in fluid communication between the preconditioning means and the means for entry of the water to the ultraviolet sterilization means for passing the preconditioned water from the preconditioning means active media to the sterilization means and for blocking the active media of the preconditioning means from entering the sterilization means whereby all water entering the ultraviolet sterilization means must pass the full length between said first and second opposed ends of the ultraviolet sterilization means and whereby both preconditioning and sterilization occur within the pressure chamber and whereby the sterilization vessel is operated under zero differential pressure.

2. Integrated apparatus for purification of water, the integrated purification apparatus including a pressure chamber having an inlet to admit water thereto for purification and an effluent outlet for the discharge of purified water therefrom; said integrated purification apparatus further including preconditioning means and ultraviolet sterilization means, the ultraviolet sterilization means being located within the pressure chamber whereby a substantially zero differential water pressure shall be present thereon and having first and second spaced apart means at respective opposed first and second ends thereof for entry of water to be sterilized and for the expulsion of water that has been sterilized; the preconditioning means including active media for purifying water, the active media being located within the pressure chamber; means for directing the water from the inlet onto the active media; segregation means at the first spaced apart means in fluid communication between the preconditioning means and the ultraviolet sterilization means for passing the preconditioned water from the preconditioning means to the ultraviolet sterilization means and for blocking the active media of the preconditioning means from entering the ultraviolet sterilization means whereby all water entering the ultraviolet sterilization means must pass the full length between said first and second opposed ends of the ultraviolet sterilization means and; the second spaced apart means for directing the water from the ultraviolet sterilization means to the effluent outlet being in fluid-tight communication with the pressure chamber effluent outlet whereby no water may pass directly to the outlet from the inlet in the absence of the active preconditioning means media and whereby the preconditioned and sterilized water shall be available for use.

3. The integrated apparatus for purification of water of claim 2 in which the ultraviolet sterilization means comprises a generally cylindrical vessel having a UV irradiation source therein and spaced apart connections for the admission and expulsion of water whereby the water passing between said admission and expulsion connections is irradiated with UV energy; the ultraviolet sterilization means vessel being located within the pressure chamber thereby placing said vessel under substantially zero differential pressure.

4. The integrated apparatus for purification of water of claim 2 in which the pressure chamber includes an aperture at one end thereof and head means rigidly mounted to said aperture for pressure sealing the aperture; the head means further including a first fluid channel, which first channel serves as said pressure chamber inlet, and a second fluid channel, which second channel serves as said pressure chamber effluent outlet.

5. The integrated apparatus for purification of water of claim 4 in which the ultraviolet sterilization means includes a UV lamp and a protective quartz sleeve and in which said head means further includes means for positioning and retaining the protective quartz sleeve and for pressure sealing said sleeve and said head means further includes means for admitting the UV lamp therethrough and into the sleeve.

* * * * *